US009844637B2

(12) United States Patent
Beduhn et al.

(10) Patent No.: US 9,844,637 B2
(45) Date of Patent: Dec. 19, 2017

(54) PROMPT APPARATUS FOR AN ANESTHESIA MACHINE AND A CORRESPONDING ANESTHESIA MACHINE

(71) Applicant: GE MEDICAL SYSTEMS GLOBAL TECHNOLOGY COMPANY, LLC., Waukesha, WI (US)

(72) Inventors: Donald Beduhn, Madison, WI (US); Lingjie Yu, WuXi (CN); Gaofeng Jiang, WuXi (CN)

(73) Assignee: GENERAL ELECTRIC COMPANY, Schenectady, NY (US)

(*) Notice: Subject to any disclaimer, the term of this patent is extended or adjusted under 35 U.S.C. 154(b) by 557 days.

(21) Appl. No.: 14/086,598

(22) Filed: Nov. 21, 2013

(65) Prior Publication Data

US 2014/0144435 A1 May 29, 2014

(30) Foreign Application Priority Data

Nov. 23, 2012 (CN) .......................... 2012 1 0481124

(51) Int. Cl.
*A61M 16/00* (2006.01)
*A61M 16/10* (2006.01)
*A61M 16/12* (2006.01)
*A61M 16/20* (2006.01)

(52) U.S. Cl.
CPC ...... *A61M 16/0051* (2013.01); *A61M 16/104* (2013.01); *A61M 16/12* (2013.01); *A61M 16/20* (2013.01); *A61M 2202/0208* (2013.01); *A61M 2202/0283* (2013.01); *A61M 2205/583* (2013.01); *A61M 2209/084* (2013.01)

(58) Field of Classification Search
CPC .................. A61M 2202/0241; H01H 2231/016
USPC ..................................... 700/265, 285; 604/24
See application file for complete search history.

(56) References Cited

U.S. PATENT DOCUMENTS

| 4,313,436 A | * | 2/1982 | Schwanbom ....... A61M 16/104 |
| | | | 128/200.19 |
| 6,106,497 A | * | 8/2000 | Wang .................. A61M 1/0084 |
| | | | 604/122 |
| 2004/0149285 A1 | | 8/2004 | Wallen |
| 2006/0150970 A1 | * | 7/2006 | Lampotang ........... A61M 16/12 |
| | | | 128/203.12 |

(Continued)

FOREIGN PATENT DOCUMENTS

| AU | 8376191 A | 3/1992 |
| CN | 101687086 A | 3/2010 |

(Continued)

OTHER PUBLICATIONS

Unofficial English Translation of Chinese Office Action issued in connection with corresponding CN Application No. 201210481124.7 dated Jan. 25, 2017.

*Primary Examiner* — (Jackie) Tan-Uyen T Ho
*Assistant Examiner* — Joseph D Boecker

(57) ABSTRACT

A signaling apparatus for an anesthesia machine, the signaling apparatus comprising an user input sub-module for receiving input information from an user, an available gas sub-module for signaling types of currently available gases according to information of the user input sub-module, and an available gas outlet sub-module for signaling currently available gas outlets according to information of the user input sub-module.

17 Claims, 4 Drawing Sheets

(56) References Cited

U.S. PATENT DOCUMENTS

| | | | |
|---|---|---|---|
| 2006/0196505 A1* | 9/2006 | Izuchukwu | A61M 16/0051 |
| | | | 128/203.15 |
| 2008/0112155 A1* | 5/2008 | Scown | B60H 1/3442 |
| | | | 362/96 |
| 2009/0206713 A1 | 8/2009 | Vilkas | |
| 2010/0175695 A1 | 7/2010 | Jamison | |
| 2010/0198200 A1* | 8/2010 | Horvath | A61B 17/00 |
| | | | 606/10 |
| 2010/0269821 A1 | 10/2010 | Larsson et al. | |
| 2011/0000488 A1* | 1/2011 | Blomberg | A61M 16/104 |
| | | | 128/203.14 |
| 2011/0088694 A1* | 4/2011 | Tobia | G01F 23/64 |
| | | | 128/204.23 |
| 2011/0297148 A1 | 12/2011 | Faber et al. | |
| 2012/0060838 A1 | 3/2012 | Laura Lapoint et al. | |
| 2013/0276780 A1* | 10/2013 | Tobia | A61M 16/0051 |
| | | | 128/202.22 |
| 2014/0150786 A1* | 6/2014 | Gongmin | A61M 16/12 |
| | | | 128/203.12 |

FOREIGN PATENT DOCUMENTS

| | | |
|---|---|---|
| CN | 102019018 A | 4/2011 |
| CN | 102309805 A | 1/2012 |
| CN | 102497904 A | 6/2012 |

* cited by examiner

PROMPT APPARATUS FOR AN ANESTHESIA MACHINE AND A CORRESPONDING ANESTHESIA MACHINE

TECHNICAL FIELD

The present invention relates to the technical field of medical devices, in particular, the technical field of anesthesia machines.

BACKGROUND OF THE INVENTION

Anesthesia machines used in hospitals usually need to provide the following three different gas outlets, namely, auxiliary gas outlet, auxiliary common gas outlet, and breathing circuit gas outlet. At any moment, only one of the three outlets is in an available state. Hence, a doctor, at any moment, needs to clearly know which gas outlet is in an available state, to ensure that gases can be provided to a patient in the manner conceived by the doctor.

The existing anesthesia machines usually adopt the structure as shown by FIG. 1 to allocate oxygen, air, and $N_2O$ as required by the doctor. That is, oxygen, air and $N_2O$ from high pressure equipment 1 are mixed via mechanic or electronic flow control valves 2, 3, 4 respectively. The mixed gases are output to gas outlets as required by the doctor via manually or electrically actuated selector valves 5 and 6 controlled by the doctor. US Patent Application Publication No. 2010/0175695 A1 also discloses an anesthesia machine structure which is improved on the basis of the structure as shown in FIG. 1.

However, the prior art including US Patent Application Publication No. 2010/0175695, does not provide a technical solution capable of timely signaling a user of an anesthesia machine what gases are mixed together currently, and which gas outlet is available.

A BRIEF SUMMARY OF THE INVENTION

An embodiment of the present invention provides a signaling apparatus for an anesthesia machine and a corresponding anesthesia machine, capable of timely and intuitively signaling a user what gases are mixed together at present, and which gas outlet is available, and solves the problem that anesthesia machines in the prior art cannot provide the user with information about available gases and available gas outlets.

According to an embodiment of the present invention, there is provided a signaling apparatus for an anesthesia machine, comprising: an user input sub-module, for receiving input information from an user; an available gas signal sub-module, for signaling types of currently available gases according to information of the user input sub-module; an available gas outlet signal sub-module, for signaling currently available gas outlets according to information of the user input sub-module.

In an embodiment, the user input sub-module comprises a transfer switch, which transfer switch is used for switching the anesthesia machine among the following gas output modes: auxiliary gas output, auxiliary common gas output and breathing circuit output.

In an embodiment, the transfer switch is a multi-channel switching valve or a single-channel switching valve.

In an embodiment, the transfer switch comprises: a first transfer switch, for selecting via switching whether the anesthesia machine will conduct auxiliary gas output; a second transfer switch, for selecting via switching whether the anesthesia machine will conduct auxiliary common gas output.

In an embodiment, the first transfer switch and the second transfer switch are mechanic switching valves or electronic switching valves.

In an embodiment, the user input sub-module is a controller that is connected with the anesthesia machine.

In an embodiment, the available gas signal sub-module comprises: an oxygen indicator, for signaling whether oxygen is available; an air indicator, for signaling whether air is available; an $N_2O$ indicator, for signaling whether $N_2O$ is available; an evaporator indicator, for signaling whether an evaporator is available.

In an embodiment, the available gas signal sub-module comprises: an oxygen indicator, for signaling whether oxygen is available; an air indicator, for signaling whether air is available; an $N_2O$ indicator, for signaling whether $N_2O$ is available; an evaporator indicator, for signaling whether an evaporator is available.

In an embodiment, the indicators provide signals according to the following relations: if the first transfer switch is configured to be in an "ON" state, no matter what state the second transfer switch is in, the oxygen indicator will signal "AVAILABLE", the $N_2O$ indicator and the evaporator indicator both will signal "NON-AVAILABLE", the air indicator will signal "NON-AVAILABLE" when the anesthesia machine is configured in a manner such that auxiliary gas output only comprises oxygen, and will signal "AVAILABLE" when the anesthesia machine is configured in a manner such that auxiliary gas output comprises oxygen and air; if the first transfer switch is configured to be in an "OFF" state, no matter what state the second transfer switch is in, the four indicators will signal "AVAILABLE".

In an embodiment, the available gas outlet signal sub-module comprises: an auxiliary gas outlet indicator, for signaling whether an auxiliary gas outlet is available; an auxiliary common gas outlet indicator, for signaling whether an auxiliary common gas outlet is available; a breathing circuit outlet indicator, for signaling whether a breathing circuit outlet is available.

In an embodiment, the available gas outlet signal sub-module comprises: an auxiliary gas outlet indicator, for signaling whether an auxiliary gas outlet is available; an auxiliary common gas outlet indicator, for signaling whether an auxiliary common gas outlet is available; a breathing circuit outlet indicator, for signaling whether a breathing circuit outlet is available.

In an embodiment, the indicators provide signals according to the following relations: when the first transfer switch and the second transfer switch both are configured to be an "OFF" state, the auxiliary gas outlet indicator and the auxiliary common gas outlet indicator will signal "NON-AVAILABLE", and the breathing circuit outlet indicator will signal "AVAILABLE"; when the first transfer switch is configured to be in an "ON" state, no matter what state the second transfer switch is in, the auxiliary gas outlet indicator will signal "AVAILABLE", and the auxiliary common gas outlet indicator and the breathing circuit outlet indicator will signal "NON-AVAILABLE"; when the first transfer switch is configured to be in an "OFF" state, and the second transfer switch is configured to be in an "ON" state, the auxiliary gas outlet indicator will signal "NON-AVAILABLE", the auxiliary common gas outlet indicator will signal "AVAILABLE", and the breathing circuit outlet indicator will signal "NON-AVAILABLE".

An embodiment of the present invention further provides an anesthesia machine, comprising the signaling apparatus for an anesthesia machine according to the present invention.

Compared with the prior art, the signaling apparatus for an anesthesia machine and the corresponding anesthesia machine, as provided by embodiments of the present invention, have the following advantageous technical effects: increasing the security of using the anesthesia machine: since the signaling apparatus is capable of signaling to a user what gases at present are mixed into the final output gases, and is capable of signaling the user which gas outlet is available, misoperations that are caused for the reason that the user may be unaware of the above information, can be avoided; and having a lower cost of realization: corresponding information can be timely, intuitively and clearly signaled to the user without making excessive modifications or adding expensive parts to the existing anesthesia machines.

DETAILED DESCRIPTION OF THE INVENTION

The present invention will be further illustrated below with reference to the drawings.

Figure 1:
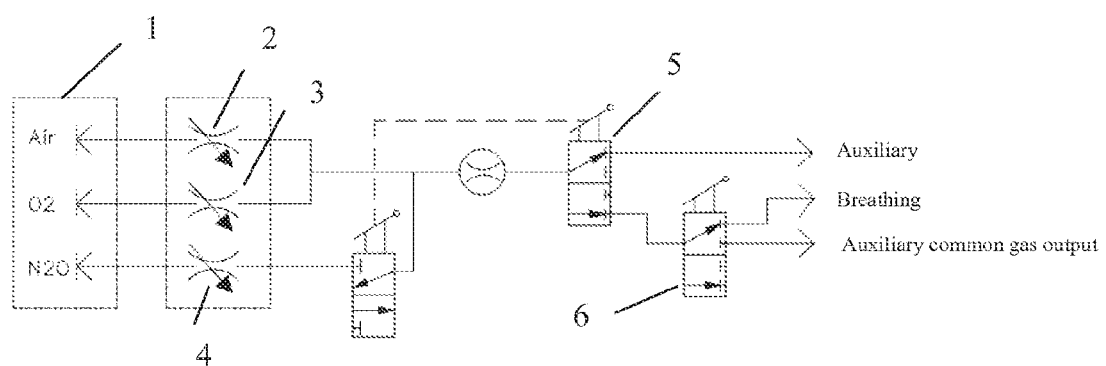
FIG. 1 is a structural diagram of an anesthesia machine in the prior art.
Figure 2:
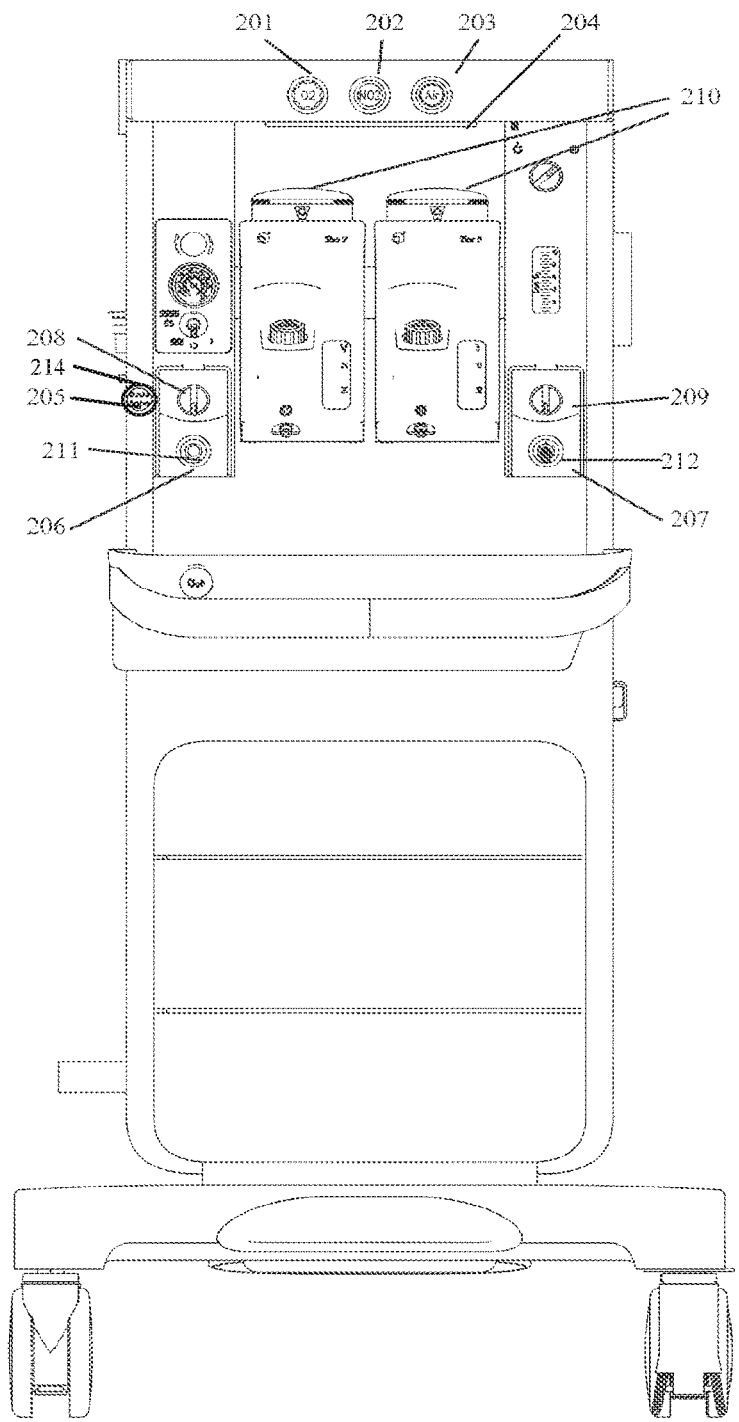
FIG. 2 is a schematic diagram of the signaling apparatus for an anesthesia machine and the corresponding anesthesia machine, according to an embodiment of the present invention.

FIG. 2 shows an overall structure of the signaling apparatus for an anesthesia machine and the corresponding anesthesia machine, as proposed by an embodiment of the present invention.

In FIG. 2, a first transfer switch 209 and a second transfer switch 208 constitute a user input sub-module; via the first transfer switch 209, a user can decide whether it is necessary to conduct auxiliary gas output, and via the second transfer switch 208, the user can decide whether it is necessary to conduct auxiliary common gas output. When both the transfer switches are turned to an "OFF" position, the anesthesia machine will conduct breathing circuit output. When both the transfer switches are turned to an "ON" position, the anesthesia machine will conduct auxiliary gas output. These two switches are not limited to mechanic switching valves, but can also be electronic switching valves.

In FIG. 2, signal lamps 201, 202, 203, 204 constitute an available gas signal sub-module, capable of indicating types of currently available gases according to the setting of states of the first transfer switch 209 and the second transfer switch 208. In order to provide the user with intuitive and clear information, an oxygen indicator 201 for signaling the available state of oxygen can be arranged near an oxygen flow control knob, e.g., an annular luminophor is adopted to surround the knob for constituting the indicator, and when oxygen is in an available state, the luminophor will be lightened or flash. Likewise, prompters 202 and 203 for signaling the available states of $N_2O$ and air are also arranged near $N_2O$ and air flow control knobs respectively, annular luminophors are adopted to surround these two knobs for constituting these two indicators, and when corresponding gases are in an available state, the luminophors will be lightened or flash. An evaporator indicator 204 for signaling the available state of an evaporator 210 is arranged just over the evaporator 210, e.g., a stripe luminophor is fixed over the evaporator, and when the evaporator 210 is in an available state, the luminophor will be lightened or flash. In other words, when the luminophor is shining or flashing, it means that the gas to which it corresponds is available, and when the luminophor goes out, it means that the gas to which it corresponds is non-available.

In FIG. 2, signal lamps 205, 206, 207 constitute an available gas outlet signal sub-module, capable of indicating currently available gas outlets according to the setting of states of the first transfer switch 209 and the second transfer switch 208. In order to provide the user with intuitive and clear information, an auxiliary gas outlet indicator 207 for signaling the available state of an auxiliary gas outlet can be arranged near an auxiliary gas outlet connector 212, e.g., an annular luminophor is adopted to surround the outlet connector 212 for constituting the indicator, and when an auxiliary oxygen outlet is in an available state, the luminophor will be lightened or flash. Likewise, an auxiliary common gas outlet indicator 206 for signaling the available state of an auxiliary common gas outlet can be arranged near an auxiliary common gas outlet connector 211, e.g., an annular luminophor is adopted to surround the outlet connector 211 for constituting the indicator, and when the auxiliary common gas outlet is in an available state, the luminophor will be lightened or flash. A breathing circuit outlet prompter 205 can also be arranged according to the same idea.

The specific working states of the signaling apparatus will be described below through several common gas output modes during the use of the anesthesia machine.

Figure 3:
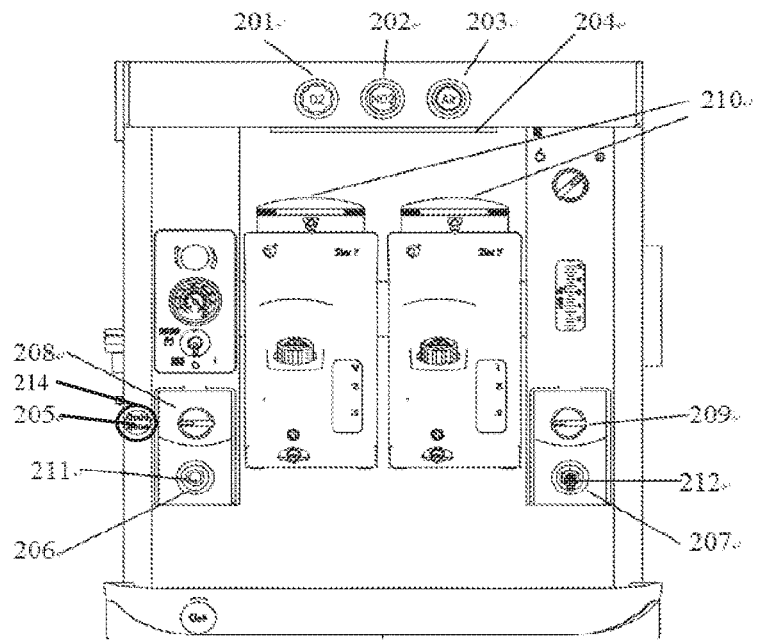
FIG. 3 is a schematic diagram of the signaling apparatus indicating breathing circuit gas output according to embodiments of the present invention.

As shown by FIG. 3, the user switches the first transfer switch 209 and the second transfer switch 208 to an "OFF" state, meaning that the anesthesia machine will conduct breathing circuit gas output. Accordingly, the oxygen indicator 201, the air indicator 203, the N20 indicator 202 and the evaporator indicator 204 in the signaling apparatus all will be lightened; meanwhile, the breathing circuit outlet indicator 205 will also be lightened, and other indicators won't be lightened. It means that the gas mixture mixed with oxygen, air and N20 will be output via the breathing circuit outlet 214 through the evaporator, carrying anesthetic gas.

Figure 4:
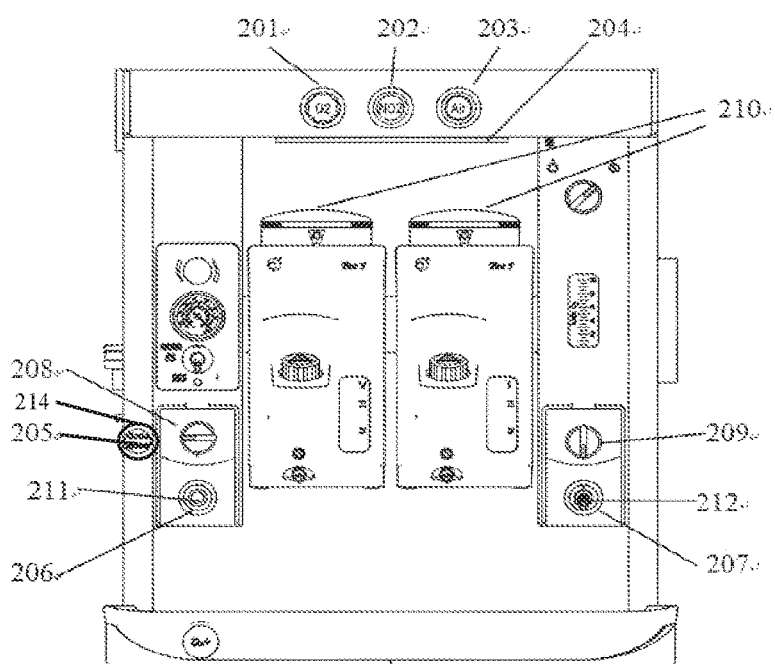
FIG. 4 is a schematic diagram of the signaling apparatus indicating auxiliary gas output according to embodiments of the present invention.

As shown by FIG. 4, the user switches the first transfer switch 209 to an "ON" state, and switches the second transfer switch 208 to an "OFF" state, meaning that the anesthesia machine will conduct auxiliary gas output. Accordingly, the oxygen indicator 201 and the air indicator 203 in the prompt apparatus will be lightened; meanwhile, the auxiliary gas outlet indicator 207 will also be lightened, and other indicators won't be lightened. It means that oxygen and air, after being mixed, jump over the evaporator, and are directly output via the auxiliary gas outlet 212.

Figure 5:
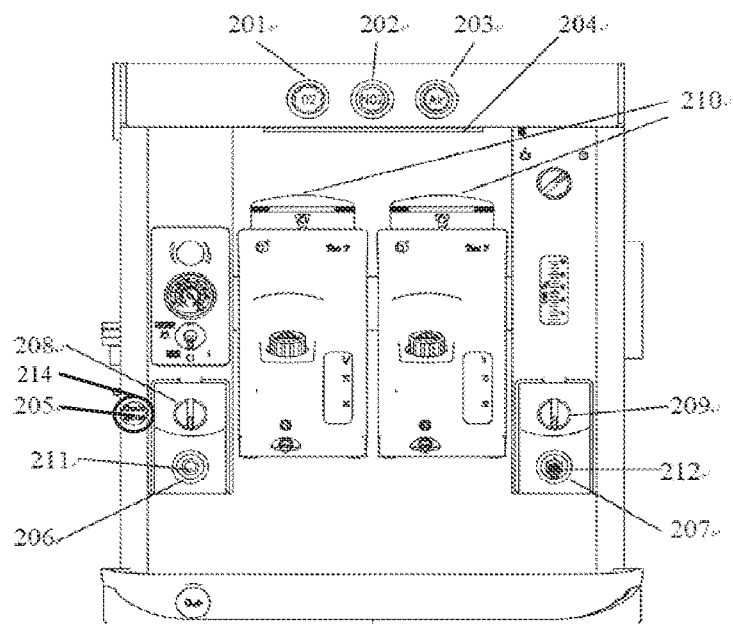
FIG. 5 is another schematic diagram of the signaling apparatus indicating auxiliary gas output according to embodiments of the present invention.

As shown by FIG. 5, the user switches the first transfer switch 209 and the second transfer switch 208 to an "ON" state, also meaning that the anesthesia machine will conduct auxiliary gas output. Accordingly, the oxygen indicator 201 and the air indicator 203 in the prompt apparatus will be lightened; meanwhile, the auxiliary gas outlet indicator 207 will also be lightened, and other indicators won't be lightened. It means that oxygen and air, after being mixed, jump over the evaporator, and are directly output via the auxiliary gas outlet 212.

It should be noted that, types of gases that are comprised in the auxiliary gas output of the existing anesthesia machines may be air plus oxygen or only oxygen; after the anesthesia machines are delivered to users, such configuration cannot be changed by the users. Hence, when prompting gas types of auxiliary gas output, the signaling apparatus will decide whether the air prompter 203 is lightened according to the factory configuration of an anesthesia machine. That is, if the auxiliary gas output gases of the anesthesia machine comprise air, the air prompt 203 will be lightened; if no air is comprised, the air indicator 203 won't be lightened.

Figure 6:
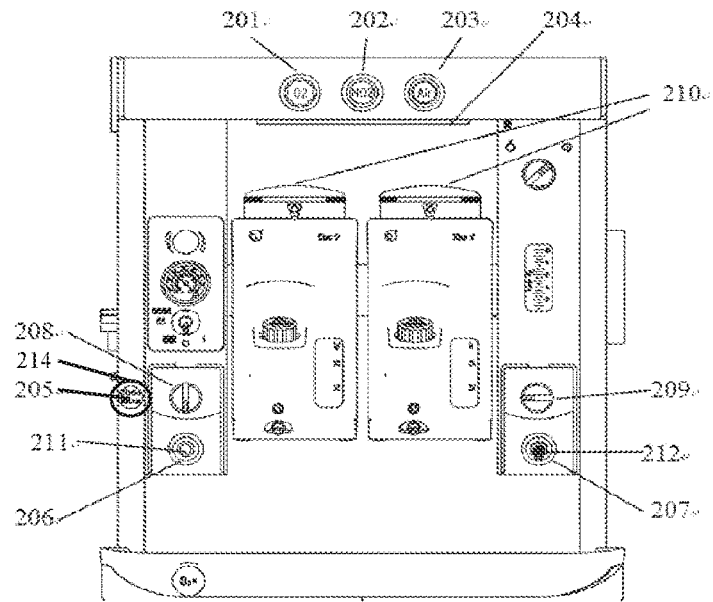
FIG. 6 is a schematic diagram of the signaling apparatus indicating auxiliary common gas output according to embodiments of the present invention.

As shown by FIG. 6, the user switches the first transfer switch 209 to an "OFF" state, and switches the second transfer switch 208 to an "ON" state, meaning that the anesthesia machine will conduct auxiliary common gas output (ACGO). Accordingly, the oxygen indicator 201, the air indicator 203, the $N_2O$ indicator 202 and the evaporator indicator 204 in the signaling apparatus all will be lightened; meanwhile, the auxiliary common gas outlet indicator 206 will also be lightened, and other indicator won't be lightened. It means that the gas mixture mixed with oxygen, air and $N_2O$ will be output via the auxiliary common gas outlet 211 through the evaporator 210, carrying anesthetic gas.

It should be indicated that, the embodiments as described above are illustrative rather than restrictive, and persons skilled in the art can work out many candidate embodiments without deviating the range of the attached claims. For example, the first transfer switch 209 and the second transfer switch 208 as described above, can be mechanic or electronic knobs; can also be built-in controllers in the anesthesia machine; can further be man-machine interfaces of other controllers (e.g., computer) that are in connection and communication with the anesthesia machine, in which the computer controls the signaling apparatus of the anesthesia machine to give a corresponding signal after the user configures the states of these two switches via the computer. In addition, these two transfer switches can further be combined into one multi-state transfer switch.

The signaling apparatus for an anesthesia machine and the corresponding anesthesia machine, as proposed by embodiments of the present invention, realize intuitive and clear signals for users with low costs, and increase the security of using the anesthesia machine.

The written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A signaling apparatus for an anesthesia machine, the signaling apparatus comprising:

a user input sub-module configured to receive input information from a user, the user input sub-module comprising a first transfer switch controlling an auxiliary gas output, the first transfer switch having a first ON state and a second OFF state, and a second transfer switch controlling an auxiliary common gas output, the second transfer switch having a first ON state and a second OFF state, wherein:
when the state of the first transfer switch is OFF and the state of the second transfer switch is OFF, the signaling apparatus controls the anesthesia machine to conduct a breathing circuit output; and
when the state of the first transfer switch is ON and the state of the second transfer switch is ON, the signaling apparatus controls the anesthesia machine to conduct an auxiliary gas output;
an available gas signal sub-module comprising indicators configured to illuminate controls for gases made available as a result of the input information of the user input sub-module; and
an available gas outlet signal sub-module comprising indicators configured to illuminate currently available gas outlets according to the input information of the user input sub-module.

2. The signaling apparatus for an anesthesia machine according to claim 1, wherein the first transfer switch and the second transfer switch comprise a multi-channel switching valve or a single-channel switching valve.

3. The signaling apparatus for an anesthesia machine according to claim 1, wherein the first transfer switch and the second transfer switch are mechanic switching valves or electronic switching valves.

4. The signaling apparatus for an anesthesia machine according to claim 1, wherein the user input sub-module is a controller connected with the anesthesia machine.

5. The signaling apparatus for an anesthesia machine according to claim 1, wherein the available gas signal sub-module comprises:
an oxygen indicator configured to signal whether oxygen is available;
an air indicator configured to signal whether air is available;
a $N_2O$ indicator, configured to signal whether $N_2O$ is available; and
an evaporator indicator configured to signal whether an evaporator is available.

6. The signaling apparatus for an anesthesia machine according to claim 5, wherein the indicators are configured to provide signals according to the following relations:
when the state of the first transfer switch is "ON", the oxygen indicator will signal "AVAILABLE", the $N_2O$ indicator and the evaporator indicator both will signal "NON-AVAILABLE", the air indicator will signal "NON-AVAILABLE" when the anesthesia machine is configured in a manner such that an auxiliary gas output only comprises oxygen, and the air indicator will signal "AVAILABLE" when the anesthesia machine is configured in a manner such that the auxiliary gas output comprises oxygen and air; and
when the state of the first transfer switch is "OFF", the oxygen indicator, the $N_2O$ indicator, the evaporator indicator and the air indicator will signal "AVAILABLE".

7. The signaling apparatus for an anesthesia machine according to claim 1, wherein the available gas outlet signal sub-module comprises:

an auxiliary gas outlet indicator configured to signal whether an auxiliary gas outlet is available;

an auxiliary common gas outlet indicator configured to signal whether an auxiliary common gas outlet is available; and a breathing circuit outlet indicator configured to signal whether a breathing circuit outlet is available.

8. The signaling apparatus for an anesthesia machine according to claim 7, wherein the signaling apparatus is configured to control the auxiliary gas outlet indicator, the auxiliary common gas outlet indicator and the breathing circuit outlet indicator to provide signals according to the following relations:

when the state of the first transfer switch and the state of the second transfer switch are "OFF", the auxiliary gas outlet indicator and the auxiliary common gas outlet indicator will signal "NON-AVAILABLE", and the breathing circuit outlet indicator will signal "AVAILABLE";

when the state of the first transfer switch is "ON", the auxiliary gas outlet indicator will signal "AVAILABLE", and the auxiliary common gas outlet indicator and the breathing circuit outlet indicator will signal "NON-AVAILABLE"; and when the state of the first transfer switch is "OFF", and the state of the second transfer switch is "ON", the auxiliary gas outlet indicator will signal "NON-AVAILABLE", the auxiliary common gas outlet indicator will signal "AVAILABLE", and the breathing circuit outlet indicator will signal "NON-AVAILABLE".

9. The signaling apparatus according to claim 1, wherein:

when the state of the first transfer switch is ON and the state of the second transfer switch is OFF, the signaling apparatus controls the anesthesia machine to conduct the auxiliary gas output; and when the state of the first transfer switch is OFF and the state of the second transfer switch is ON, the signaling apparatus controls the anesthesia machine to conduct an auxiliary common gas output.

10. The signaling apparatus for an anesthesia machine according to claim 1, wherein when the state of the first transfer switch is OFF and the state of the second transfer switch is OFF, the signaling apparatus controls the anesthesia machine to:

light an oxygen indicator for an oxygen control, an air indicator for an air control, an N2O indicator for an N2O control, and a breathing circuit outlet indicator; and to not light an auxiliary gas outlet indicator and an auxiliary common gas outlet indicator.

11. The signaling apparatus for an anesthesia machine according to claim 1, wherein when the state of the first transfer switch is ON and the state of the second transfer switch is ON, the signaling apparatus controls the anesthesia machine to:

light an oxygen indicator for an oxygen control, an air indicator for an air control, and an auxiliary gas outlet indicator; and to not light an N2O indicator for an N2O control, a breathing circuit outlet indicator, and an auxiliary common gas outlet indicator.

12. An anesthesia machine, comprising:

a plurality of different gas outlets;

a signaling apparatus configured to control a flow of a gas to each of the plurality different gas outlets, the signaling apparatus comprising:

a user input sub-module configured to receive input information from a user, the user input sub-module comprising a first transfer switch controlling an auxiliary gas output, the first transfer switch having a first ON state and a second OFF state, and a second transfer switch controlling an auxiliary common gas output, the second transfer switch having a first ON state and a second OFF state, wherein:

when the state of the first transfer switch is OFF and the state of the second transfer switch is OFF, the signaling apparatus controls the anesthesia machine to conduct a breathing circuit output; and when the state of the first transfer switch is ON and the state of the second transfer switch is ON, the signaling apparatus controls the anesthesia machine to conduct an auxiliary gas output;

an available gas signal sub-module comprising a first plurality of signal lamps configured to illuminate controls for gases made available as a result of the input information of the user input sub-module; and an available gas outlet signal sub-module comprising a second plurality of signal lamps configured to signal currently available gas outlets according to the input information of the user input sub-module.

13. The anesthesia machine according to claim 12, wherein the first transfer switch and the second transfer switch comprise a multi-channel switching valve or a single-channel switching valve.

14. The anesthesia machine according to claim 12, wherein the available gas signal sub-module comprises:

an oxygen indicator configured to signal whether oxygen is available;

an air indicator configured to signal whether air is available;

a $N_2O$ indicator configured to signal whether $N_2O$ is available; and an evaporator indicator configured to signal whether an evaporator is available.

15. The anesthesia machine according to claim 14, wherein the signaling apparatus is configured to control the oxygen indicator, the air indicator, the $N_2O$ indicator and the evaporator indicator to provide signals according to the following relations:

when the state of the first transfer switch is "ON" the oxygen indicator will signal "AVAILABLE", the $N_2O$ indicator and the evaporator indicator both will signal "NON-AVAILABLE", and the air indicator will signal "NON-AVAILABLE" when the anesthesia machine is configured in a manner such that an auxiliary gas output only comprises oxygen, and the air indicator will signal "AVAILABLE" when the anesthesia machine is configured in a manner such that the auxiliary gas output comprises oxygen and air; and when the state of the first transfer switch is "OFF" state the oxygen indicator, the air indicator, the $N_2O$ indicator and the evaporator indicator will signal "AVAILABLE".

16. The anesthesia machine according to claim 12, wherein the available gas outlet signal sub-module comprises:

an auxiliary gas outlet indicator configured to signal whether an auxiliary gas outlet is available;

an auxiliary common gas outlet indicator configured to signal whether an auxiliary common gas outlet is available; and a breathing circuit outlet indicator configured to signal whether a breathing circuit outlet is available.

17. The anesthesia machine according to claim 12, wherein the first plurality of signal lamps comprise annular luminophores that are configured to surround the controls for the gasses made available as a result of the input information of the user input sub-module.

\* \* \* \* \*